United States Patent
Kim et al.

(10) Patent No.: US 9,271,629 B2
(45) Date of Patent: Mar. 1, 2016

(54) FREQUENCY DOMAIN OPTICAL COHERENCE TOMOGRAPHY IMAGE NOISE REDUCTION BY SUBTRACTION OF ADJACENT DEPTH DATA

(75) Inventors: Ji Hyun Kim, Incheon (KR); Jichai Jeong, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 384 days.

(21) Appl. No.: 13/480,209

(22) Filed: May 24, 2012

(65) Prior Publication Data

US 2013/0135624 A1    May 30, 2013

(30) Foreign Application Priority Data

Nov. 24, 2011    (KR) .................. 10-2011-0123691

(51) Int. Cl.
  *G01B 9/02*    (2006.01)
  *A61B 1/00*    (2006.01)

(52) U.S. Cl.
  CPC .......... *A61B 1/00009* (2013.01); *G01B 9/0207* (2013.01); *G01B 9/02044* (2013.01); *G01B 9/02087* (2013.01)

(58) Field of Classification Search
  CPC ........... G01B 9/02085; G01B 9/02087; G01B 9/02091; G01B 11/0675; G01B 9/0207; G01B 9/02044; A61B 3/102; A61B 5/0066; A61B 1/00009
  USPC ................................. 356/479, 497
  See application file for complete search history.

(56) References Cited

U.S. PATENT DOCUMENTS 8,144,381 B2 * 3/2012 Nakahata .................. 359/216.1
2004/0239946 A1 * 12/2004 Kane et al. ................ 356/497

FOREIGN PATENT DOCUMENTS

JP    2009523564 A    6/2009
KR    10-2006-0120165    11/2006
KR    10-2011-0036593    4/2011

OTHER PUBLICATIONS

Office Action for KR Application No. 10-2011-0123691 with English translation.
Ji Hyun Kim et al., "Reduction Technique of Fixed Pattern Noise using Subtracting Self-reference Spectrum for FD-OCT System," vol. 18, No. 1, COOC 2011, May 26, 2011.

* cited by examiner

*Primary Examiner* — Hwa Lee
(74) *Attorney, Agent, or Firm* — McDermott Will & Emery LLP

(57) ABSTRACT

An information processing apparatus for frequency domain optical coherence tomography comprises an image scanning unit that receives measurement data from an optical coherence tomography device, while moving a measurement point to the next adjacent point at each measurement time by controlling the optical coherence tomography device, and generates depth information based on the measurement data to produce a raw tomographic image. The apparatus includes a noise reduction unit that reduces noise from the raw tomographic image to produce a result tomographic image. The noise reduction unit reduces the noise from the raw tomographic image by subtracting the depth information generated by the image scanning unit at each measurement time from the depth information generated at another measurement time adjacent to said each measurement time.

12 Claims, 8 Drawing Sheets

$$g(z,t) = g_{raw}(z,t) - g_{raw}(z,t-1)$$
$$= g_{image}(z,t) - g_{image}(z,t-1) + n(z,t) - n(z,t-1)$$
$$= g_{image}(z,t) - g_{image}(z,t-1)$$
$$\triangleq g_{image}(z,t)$$

where $n(z,t) \approx n(z,t-1)$ $n(z,t) - n(z,t-1) \approx 0$

(a) REFERENCE SPECTRUM SUBTRACTION (b) MEAN-LINE SUBTRACTION

(c) MEDIAN-LINE SUBTRACTION

(d) NOISE REDUCTION METHOD IN ACCORDANCE WITH PRESENT DISCLOSURE

FIG. 7

(a) REFERENCE SPECTRUM SUBTRACTION (b) MEAN-LINE SUBTRACTION (c) MEDIAN-LINE SUBTRACTION (d) NOISE REDUCTION METHOD IN ACCORDANCE WITH PRESENT DISCLOSURE

FREQUENCY DOMAIN OPTICAL COHERENCE TOMOGRAPHY IMAGE NOISE REDUCTION BY SUBTRACTION OF ADJACENT DEPTH DATA

CROSS-REFERENCE TO RELATED APPLICATION

This application claims the benefit of Korean Patent Application No. 10-2011-0123691 filed on Nov. 24, 2011, the entire disclosures of which are incorporated herein by reference.

FIELD OF THE INVENTION

The present disclosure relates to an information processing apparatus and a method for optical coherence tomography and more specifically, relates to an information processing apparatus and a method for frequency domain optical coherence tomography.

BACKGROUND OF THE INVENTION

Frequency domain or Fourier domain optical coherence tomography (FD-OCT) is an advanced tomography technology widely used in the medical diagnostic field. In particular, because the FD-OCT technology makes it possible to safely obtain tomographic images of retina and others, it is popular in the ophthalmology field, and is also used for coronary artery diagnosis or for endoscopy.

In addition to the medical field, the FD-OCT technology has also been used in various industrial fields, for example, measuring a thickness of a wafer and analyzing each layer of a picture to preserve the artwork. Optical-fiber-based optical coherence tomography is particularly useful not only for medial endoscopy but also for an industrial use, because it can be used in a hard-to-reach area such as radioactive contaminated environments.

The optical coherence tomography has a superior resolution compared to conventional medical imaging technologies such as MRI (Magnetic Resonance Imaging). Furthermore, FD-OCT has a good signal-to-noise ratio and is fast in measurement.

However, tomographic images generated using FD-OCT are susceptible to fixed horizontal stripe noise due to the DC spectrum of a light source. Thus, there have been researches for reducing such fixed pattern noise.

For example, a reference spectrum subtraction method reduces noise by obtaining the frequency spectrum of an optical power in a physical way and subtracting it from the depth information. However, this method is inconvenient due to the necessity for obtaining the DC spectrum of the light source before a sample scanning.

Some techniques that use software for subtracting fixed stripe noise has been introduced to solve the above inconveniences. Of those techniques, a mean-line subtraction method calculates the mean of the signals and subtracts the mean from each depth information signal. The median-line subtraction method is similar to the mean-line subtraction method except that it uses the median of the signals instead of the mean of the signals.

However, in the above-described conventional methods, if the intensity of the light source changes during measurement, i.e. while the depth information is obtained, noise cannot be reduced normally, which becomes a big problem particularly when an optical fiber is used for optical coherence tomography. By way of example, in the case of medial endoscopy, the intensity of the light source can fluctuate dynamically due to external circumstances such as heartbeats, blood circulation, and breathing. In particular, when an endoscopic tube is bent in a blood vessel, it can cause radical fluctuations in the light source.

Therefore, a need exists for providing an apparatus and a method for efficiently reducing noise, when an unstable light source is used or when the light source is fluctuating dynamically in an optical-fiber-based environment such as an endoscope.

In this regard, Korean Patent Laid-open Publication No. 10-2011-0036593 (entitled "Imaging apparatus and imaging method using optical coherence tomography, and computer readable storing medium") discloses an apparatus and method for reducing noise caused by a return light.

Also, Korean Patent Laid-open Publication No. 10-2006-0120165 (entitled "Method and apparatus for performing optical imaging using frequency-domain interferometry") discloses an apparatus and method for reducing shot noise.

BRIEF SUMMARY OF THE INVENTION

An object of the present invention is to solve the problem of fixed pattern noise generated in frequency domain optical coherence tomography, and the illustrative embodiments provide an information processing apparatus and method for optical coherence tomography capable of rapidly and efficiently reducing fixed pattern noise.

An aspect of the present disclosure provides an information processing apparatus for frequency domain optical coherence tomography comprising an image scanning unit that receives measurement data from the optical coherence tomography device, while moving the measurement point to the next adjacent point at each measurement time by controlling the optical coherence tomography device, and generates depth information based on the measurement data to produce a raw tomographic image. The information processing apparatus further comprises a noise reduction unit that reduces noise from the raw tomographic image to produce a result tomographic image, wherein the noise reduction unit reduces the noise from the raw tomographic image by subtracting the depth information generated by the image scanning unit at each measurement time from the depth information generated at another measurement time adjacent to said each measurement time.

A second aspect of the present disclosure encompasses an information processing method for frequency domain optical coherence tomography. The method produces a raw tomographic image by receiving the measurement data from the optical coherence tomography device, while moving the measurement point to the next adjacent point at each measurement time by controlling the optical coherence tomography device, and generating depth information based on the measurement data. The method produces a result tomographic image by reducing noise from the raw tomographic image. The production of the result tomographic image comprises reducing the noise from the raw tomographic image by subtracting the depth information generated by the image scanning unit at each measurement time from the depth information generated at another measurement time adjacent to said each measurement time.

The information processing apparatus and method for optical coherence tomography can rapidly and efficiently reduce fixed pattern noise from tomographic images.

Also, the fixed pattern noise can be reduced even when the intensity of the light source fluctuates dynamically.

Furthermore, the fixed pattern noise can be reduced without having to change the hardware configuration or having to perform any additional calculation using hardware.

Moreover, the fixed pattern noise can be reduced without overhead by performing only a simple operation such as a subtraction of matrices.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and therefore, do not intend to limit its scope, the disclosure will be described with specificity and in detail through use of the accompanying drawings, in which.

DETAILED DESCRIPTION OF THE INVENTION

Hereinafter, embodiments of the present disclosure will be described in detail with reference to the accompanying drawings so that the present disclosure may be readily implemented by those skilled in the art. However, the present disclosure is not limited to the embodiments but can be embodied in various other ways. In drawings, parts irrelevant to the description are omitted for the simplicity of explanation, and like reference numerals denote like parts through the whole document.

Through the whole document, the terms "connected to" or "coupled to" that are used to designate a connection or coupling of one element to another element includes both a case that an element is "directly connected or coupled to" another element and a case that an element is "electronically connected or coupled to" another element via still another element. Further, the terms "comprises or includes" and/or "comprising or including" used in the document mean that one or more other components, steps, operation and/or existence or addition of elements are not excluded in addition to the described components, steps, operation and/or elements unless context dictates otherwise.

Figure 1:
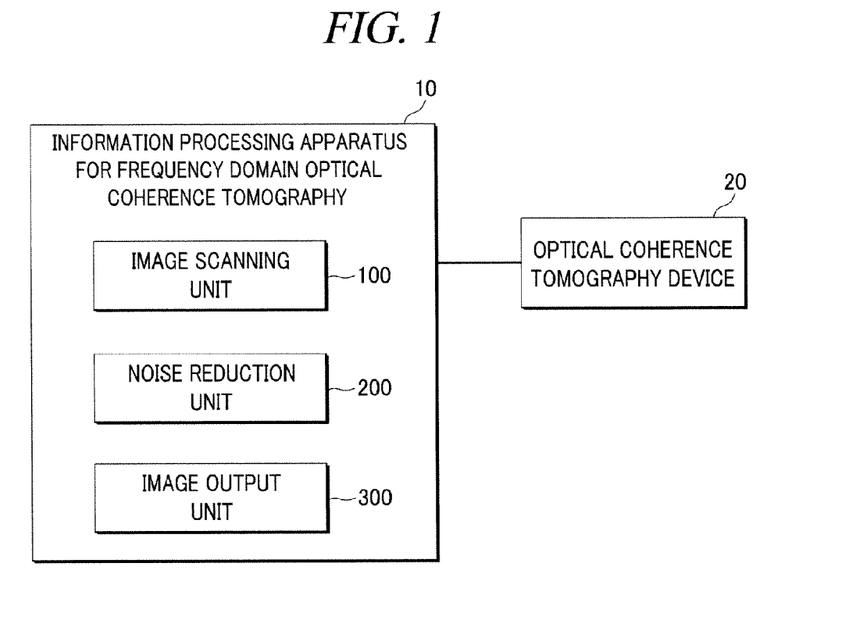
FIG. 1 is a block diagram illustrating an information processing apparatus for optical coherence tomography in accordance with an illustrative embodiment.

FIG. 1 is a block diagram illustrating an information processing apparatus for optical coherence tomography in accordance with an illustrative embodiment.

The information processing apparatus for optical coherence tomography 10 is connected with an optical coherence tomography device 20 to form an FD-OCT (frequency domain or Fourier domain optical coherence tomography) system.

The information processing apparatus for optical coherence tomography 10 is not limited to any particular methods of FD-OCT. For example, the information processing apparatus for optical coherence tomography 10 in accordance with the present disclosure can be applied to either frequency domain optical coherence tomography using a spectrometer or swept source optical coherence tomography (SS-OCT).

The information processing apparatus for optical coherence tomography 10 includes an image scanning unit 100 configured to produce a raw tomographic image 510 by performing a lateral scan and a noise reduction unit 200 configured to reduce noise 520 from the raw tomographic image 510 to produce a result tomographic image 540. Details thereof will be provided later.

The information processing apparatus for optical coherence tomography 10 may further include an image output unit 300 configured to output the tomographic image. In general, the image output unit 300 outputs the result tomographic image 540 in which the noise 520 is reduced, but it may output the raw tomographic image 510 if necessary.

Now, before providing the details of the information processing apparatus for optical coherence tomography 10 in accordance with the present illustrative embodiment, components of the optical coherence tomography device 20 will be roughly explained with reference to FIG. 2.

Figure 2:
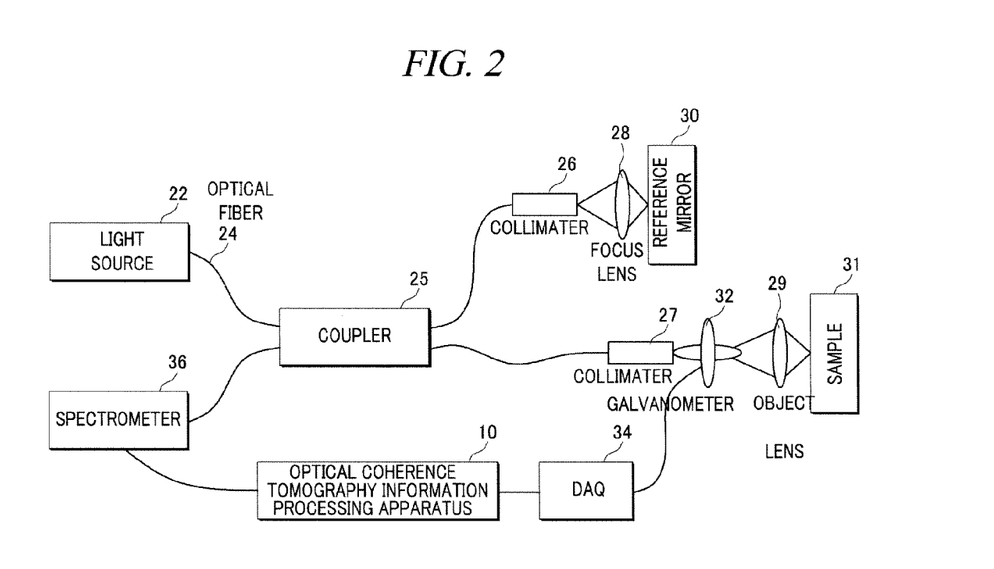
FIG. 2 illustrates an optical coherence tomography system using the apparatus of FIG. 1.

FIG. 2 illustrates an embodiment of optical fiber based frequency domain optical coherence tomography system using the information processing apparatus for optical coherence tomography 10.

The optical coherence tomography device 20 includes a sample 31 to be positioned on the target object side of the device, a reference mirror 30, a focus lens 28, an object lens 29, collimaters 26 and 27, a coupler 25, a galvanometer 32, a light source 22, a spectrometer 36, and a DAQ (data acquisition unit) 34. For the light source 22, for example, a superluminescence diode (SLD) may be used.

Configurations of the optical coherence tomography device 20 are well disclosed in conventional techniques, thus, details thereof will be skipped here and the explanations will be focused on the components related to the information processing apparatus for optical coherence tomography 10.

The spectrometer 36 and the DAQ 34 of the optical coherence tomography device 20 are connected to the information processing apparatus for optical coherence tomography 10 in accordance with the present illustrative embodiment through a communication and/or control means (for example, an USB). By way of example, the information processing apparatus for optical coherence tomography 10 can shift the measurement point by sending a control command to move the galvanometer 32. Also, the information processing apparatus for optical coherence tomography 10 can receive measured spectrum information from the spectrometer 36.

In the present illustrative embodiment, each component of the optical coherence tomography device 20 is connected via an optical fiber 24. Such embodiment is usually used for endoscopy, in which the light source 22 may fluctuate significantly and noise, in turn, tend to be easily generated. By way of example, when the optical fiber is bent while moving along a blood vessel, the light source 22 may fluctuate radically.

As described above, in the conventional techniques, when the light source varies dynamically, it is not easy to reduce the noise but the information processing apparatus for optical coherence tomography 10 in accordance with the present illustrative embodiment can easily reduce, in real time, the noise caused by the radical fluctuations of the light source 22 occurring when the optical fiber 24 is bent.

Figure 3:
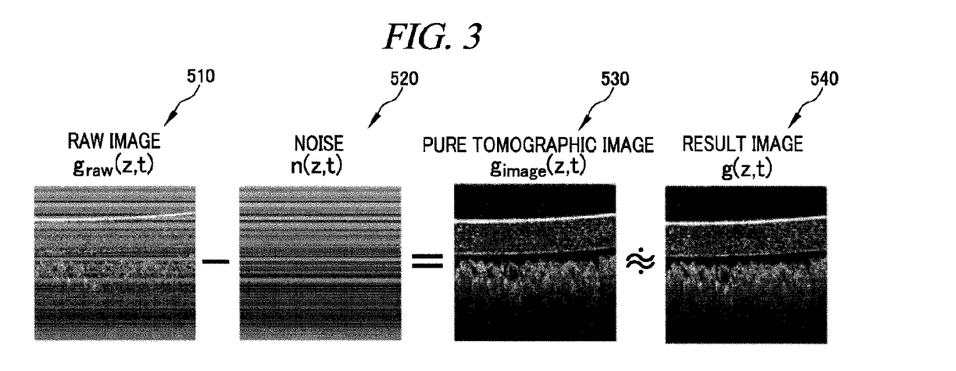
FIG. 3 shows the relationship between a tomographic image and its noise.

FIG. 3 shows the relationship between a tomographic image and its noise.

The raw tomographic image 510 is an image produced by the image scanning unit 100. The image scanning unit 100 of the information processing apparatus for optical coherence tomography 10 in accordance with the present illustrative embodiment produces depth information per each measurement point through an A-scan and combines the obtained depth information laterally to perform a B-scan. In other words, the image scanning unit 100 receives the measurement data from the optical coherence tomography device 20, while moving the measurement point to the next adjacent point at each measurement time by controlling the optical coherence tomography device 20, and produces the depth information by performing an equal interval K-space transform and an inverse Fourier transform on the received spectrum data.

The raw tomographic image 510 produced by this lateral scan is an image that contains depth information z at each measurement time t (graw (z, t)). That is, represents the axial position in each A-line and t denotes each A-line number.

However, as described above, in frequency domain optical coherence tomography, fixed pattern noise (for example, stripe patterns) usually occurs in the images due to the offset of the image signal caused by the DC-spectrum of the light source 22. Therefore, the raw tomographic image 510 produced by the image scanning unit 100 is an image in which the noise 520 is added to the pure tomographic image 530 that purely represents only the cross sectional image of the target object.

As shown in the illustrative embodiment depicted in FIG. 3, if there is too much noise in the raw tomographic image 510, the cross section of the target object can become hardly distinguishable. Therefore, it is necessary to reduce the noise 520 from the raw tomographic image 510 to obtain a clear view of the cross section as can be seen in the pure tomographic image 530.

Therefore, as depicted in FIG. 3, the noise reduction unit 200 of the information processing apparatus for optical coherence tomography 10 in accordance with the present illustrative embodiment reduces the noise 520 from the raw tomographic image 510 obtained by the image scanning unit 100, so that the result tomographic image 540 close to the pure tomographic image 530 can be produced.

Figure 4:
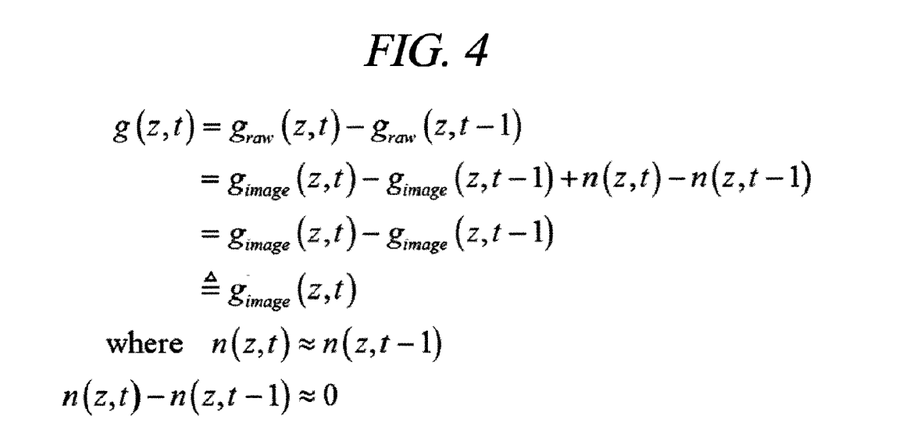
FIG. 4 shows an equation that provides a basis for a method of reducing noise in accordance with the present disclosure.

As shown in the equation depicted in FIG. 4, the noise reduction unit 200 of the information processing apparatus for optical coherence tomography 10 in accordance with the present illustrative embodiment can produce the result tomographic image 540 close to the pure tomographic image 530.

Unlike the conventional techniques, the present disclosure can reduce the noise 520 even when the light source 22 fluctuates dynamically because it only needs to subtract the measurement value at each measurement time from the measurement value at an adjacent measurement time without having to calculate any representative value (for example, mean or median) of all the measurement values.

The result tomographic image 540 can be produced by subtracting the depth information of the raw tomographic image 510 measured at the measurement time t-1 from the depth information of the raw tomographic image 510 measured at the measurement time t (refer to the first line of the equation).

Since the raw tomographic image 510 is the pure tomographic image 530 with additional the noise 520, it will be understood that the raw tomographic image 510 at the measurement times t and t-1 can be substituted with the pure tomographic image 530 together with the noise 520 at the measurement times t and t-1, and then the result tomographic image 540 should be equal to the pure tomographic image 530 and the noise 520 at the measurement time t-1 subtracted from the pure tomographic image 530 and the noise 520 at the measurement time t (refer to the second line of the equation).

Since the noise 520 has a fixed pattern, the noise 520 at the measurement time t is almost the same as the noise 520 at the measurement time t-1 (refer to the "where" part of the equation). Therefore, the result tomographic image 540 is substantially equal to the pure tomographic image 530 at the measurement time t subtracted from the pure tomographic image 530 at the measurement time t-1 (refer to the third line of the equation) and, in turn, is substantially equal to the pure tomographic image 530 (refer to the fourth line of the equation).

Therefore, the result tomographic image 540, produced by subtracting the depth information of the raw tomographic image 510 at the measurement time t from the depth information of the raw tomographic image 510 at the measurement time t-1, becomes substantially the same as the pure tomographic image 530. Conclusively, it is proved that with a simple subtraction of the depth data measured at adjacent measurement times (t and t-1, or t+1 and t), a clear image without fixed pattern noise can be produced.

As described above, the noise reduction unit 200 can reduce the noise 520 clearly by only subtraction of measurement data at adjacent measurement times. Furthermore, the noise reduction unit 200 uses a matrix form for efficiently performing such an operation.

Figure 5:
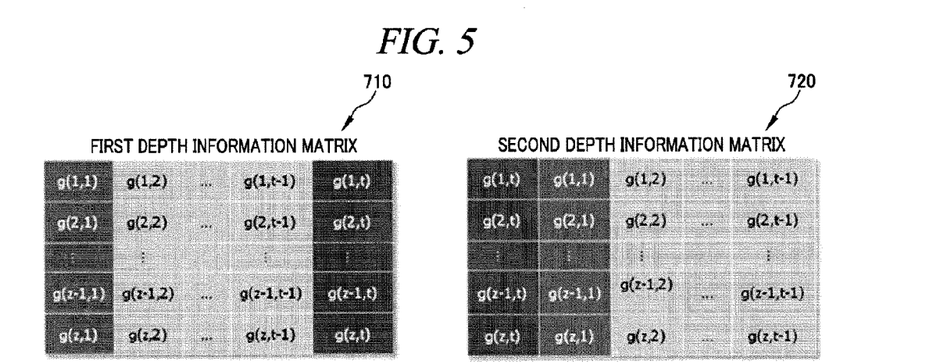
FIG. 5 shows exemplary embodiments of the first and second depth information matrices in accordance with the present disclosure.

FIG. 5 shows exemplary embodiments of the first and second depth information matrices in accordance with the present disclosure.

The raw tomographic image 510 contains the depth information z at the measurement time t. Thus, it can be expressed in the form of a two-dimensional matrix which is referred to as the first depth information matrix 710 here. In FIG. 5, columns of the matrix represent the measurement times and rows of the matrix represent the depth information at each measurement time. The rows may represent the measurement times and the columns may represent the depth information.

By circularly shifting the columns or the rows of the first depth information matrix 710 per measurement time, a second depth information matrix 720 can be obtained. That is, the second depth information matrix 720 is a matrix generated by shifting each measurement datum at each measurement time of the first depth information matrix 710 to its adjacent location.

FIG. 5 depicts an embodiment, which generates the second depth information matrix 720 by inserting the last column of the first depth information matrix 710 into the front column and shifting each of the other columns to the next column accordingly. If the rows represent the measurement times and the columns represent the depth information, the rows can be circularly shifted.

Here, the subtraction of the measurement data at time t and the measurement data at time t-1 can be extended to the subtraction of the measurement data at time t-1 and the measurement data at time t-2. In other words, when the rows or the columns in the first depth information matrix 710 are circularly shifted, it is possible to shift them two by two as well as one by one.

When a subtraction is applied to these two matrices, each element of the result matrix will be a value obtained by subtraction of the depth information produced by the image scanning unit 100 at each measurement time and the depth information produced at an adjacent measurement time. This is not applicable to the foremost column. However, it does not deserve notice, since the edges of an image are not important.

This result matrix is the result tomographic image 540. Therefore, the noise-reduced result tomographic image 540 is produced by a simple operation such as a subtraction of matrices. Thus, the method for reducing noise in accordance with the present disclosure is fast and has low overhead.

Figure 6:
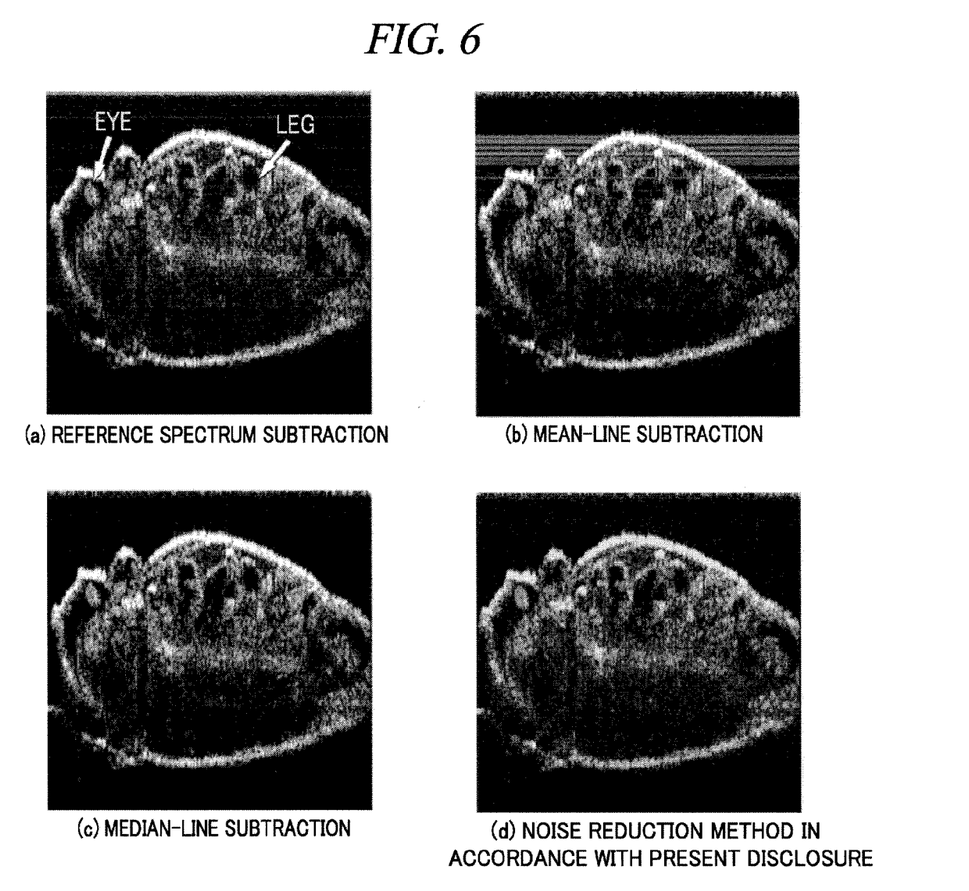
FIG. 6 shows an exemplary noise-reduced tomographic image in accordance with the present disclosure, provided with comparable noise-reduced images according to various conventional methods.
Figure 7:
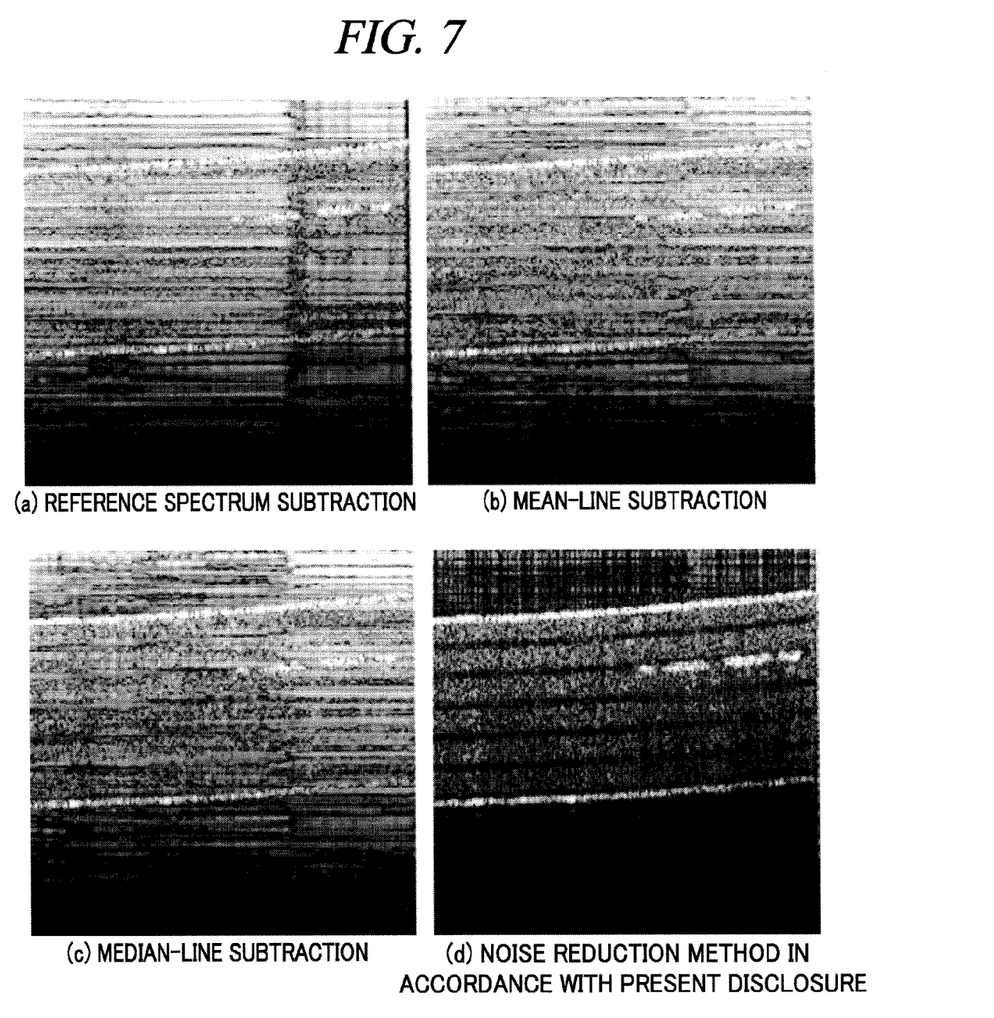
FIG. 7 shows an exemplary noise-reduced tomographic image in accordance with the present disclosure, provided with comparable noise-reduced images according to various conventional methods.
Figure 8:
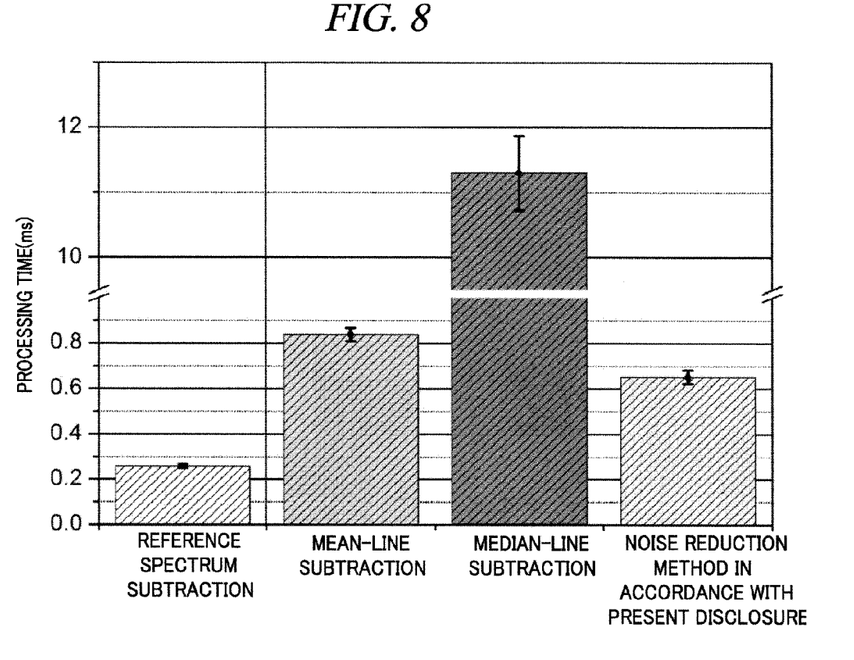
FIG. 8 shows an example of the processing speed of the noise reduction method in accordance with the present disclosure, provided with those of various conventional methods for comparison.

FIGS. 6, 7, and 8 show examples of the result image and the processing speed of the noise reduction method in accordance with the present disclosure, provided with those of various conventional methods for comparison As depicted in FIGS. 6 to 8, the performance and speed of the noise reduction method in accordance with the present illustrative embodiment is better than those of any prior art. Even better, as described above and as shown in the diagrams, even when the light source 22 fluctuates dynamically, the noise reduction performance of the present disclosure is not much affected.

This can be seen well in FIG. 7. FIG. 7 depicts tomographic images, of a multi-layered polymer phantom, obtained by various methods in an optical-fiber-based environment to show how well each noise reduction method reduces noise under unstable environments such as an endoscopic system used for a human body. As illustrated in FIG. 7, when the optical fiber is bent and the light source continuously fluctuates during the lateral scan, the noise reduction method in accordance with the present illustrative embodiment shows the best performance in reducing noise.

Figure 9:
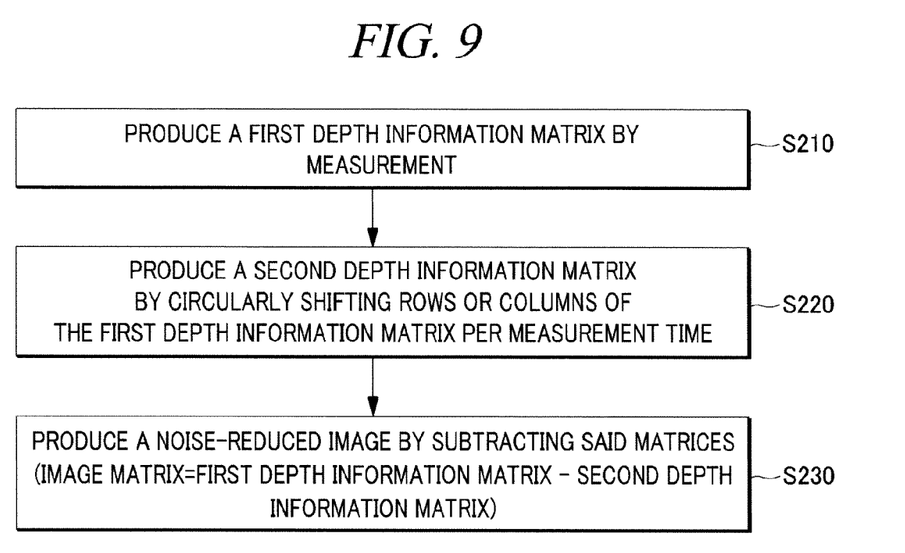
FIG. 9 shows a flow of the information processing method for optical coherence tomography in accordance with the present disclosure.

Now, referring to FIG. 9, explanations will be provided with respect to a flow diagram of an information processing method for optical coherence tomography in accordance with the present disclosure.

By measurement, produced is the raw tomographic image 510, i.e., the first depth information matrix 710 which contains the depth information of a cross section of a target object measured at each measurement time (S210).

Then, the rows or columns of the first depth information matrix 710 per measurement time are circularly shifted to generate the second depth information matrix 720 (S220).

Then, the noise-reduced result tomographic image 540 is produced by subtraction of matrices(S230). That is, the result tomographic image 540 is a matrix obtained by subtracting the second depth information matrix 720 from the first depth information matrix 710 or vice versa.

Figure 10:
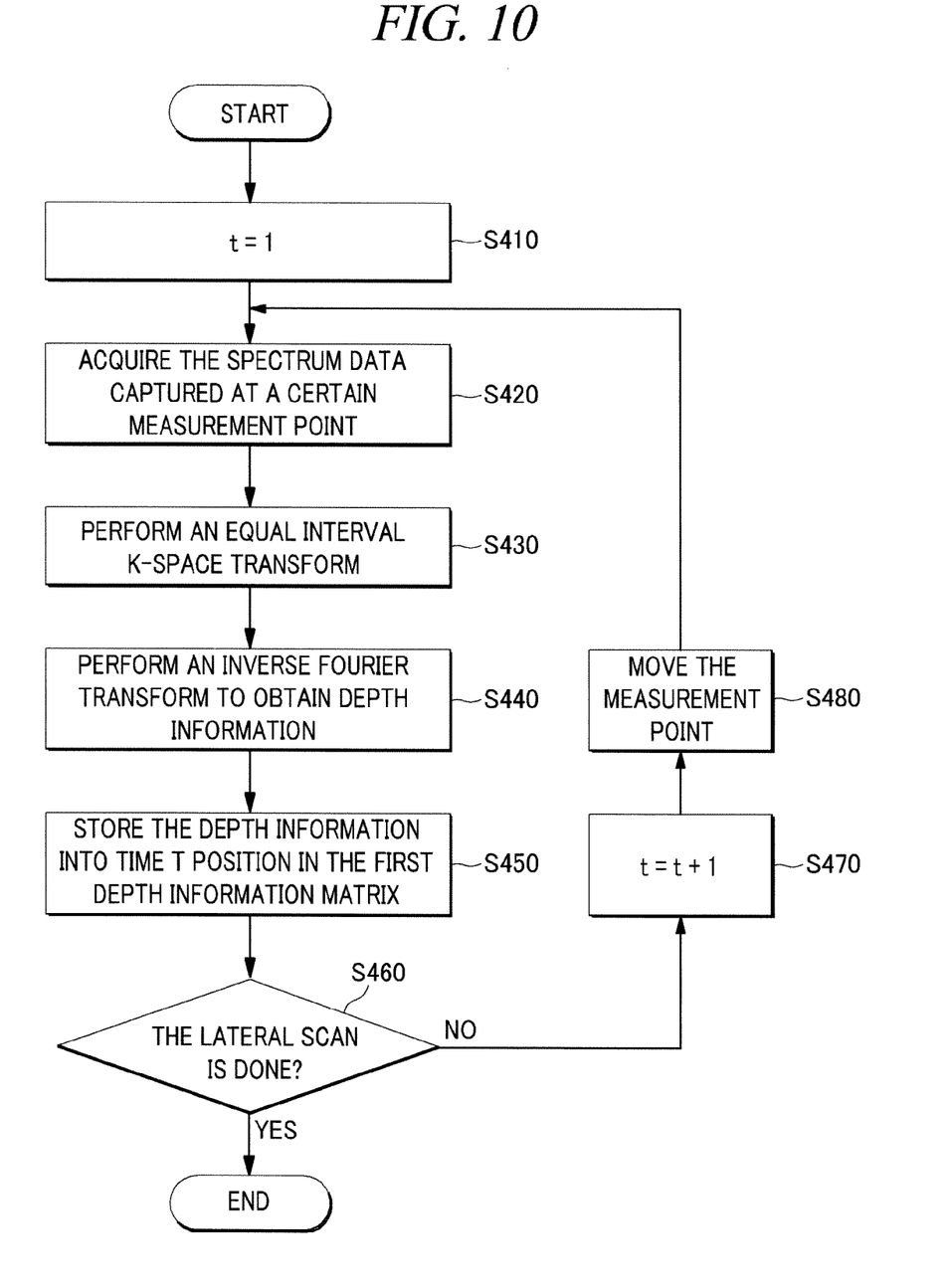
FIG. 10 shows a flow of the process for generating a raw tomographic image in accordance with the present disclosure.

FIG. 10 shows a flow diagram of the first depth information matrix 710 generation process (S210).

The measuring process is started (S410) by the information processing apparatus for optical coherence tomography 10 controlling the optical coherence tomography device 20 to set its measurement point at a starting point. By way of example, the galvanometer 32 can be positioned at an edge of the sample 31. Note that, the initial value of t, which denotes the measurement time, may be any other number than 1 as shown in the embodiment of FIG. 10.

On receiving the spectrum information at the measurement point from the optical coherence tomography device 20 (S420), an equal interval K-space transform and an inverse Fourier transform are performed to obtain the depth information (s430 and S440, respectively). The obtained depth information is stored into the corresponding position assigned for time point t in the first depth information matrix 710 (S450). In other words, an A-scan is performed at each measurement time t. During this operation, a temporary storage such as a buffer can be used.

The measurement time and the measurement point are shifted by one step, (S470 and S480, respectively).

The above-described processes are repeated until the lateral scan (i.e. B-scan) is completed (S460).

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. An information processing apparatus to generate a frequency domain optical coherence tomography image, which is connected with an optical coherence tomography device, the information processing apparatus comprising:
    a processor;
    a memory; and
    a program stored in the memory to be executed by the processor,
    wherein the program includes instructions which, when executed, causes the processor to perform the following acts:
    control the optical coherence tomography device to shift a measurement point to a next adjacent measurement point at each measurement time and to acquire a measurement data at each measurement time by sending a control command to move a galvanometer of the optical coherence tomography device,
    receive the measurement data from a spectrometer of the optical coherence tomography device,
    generate a depth based on the measurement data,
    generate a raw tomographic image from the depth, and
    generate a result tomographic image by reducing noise from the raw tomographic image,
    wherein the act to generate the result tomographic image comprises:
    subtracting the depth at each measurement time from the depth generated at another measurement time adjacent to said each measurement time, and
    wherein the result tomographic image is an image in which the fixed pattern noise of the raw tomographic image is reduced.

2. The apparatus of claim 1, wherein the program includes instructions which, when executed, causes the processor to output the result tomographic image.

3. The apparatus of claim 1,
    wherein the raw tomographic image and the result tomographic image are images containing the depth measured at each measurement time.

4. The apparatus of claim 1,
wherein the raw tomographic image and the result tomographic image are expressed in matrices in which each element represents the depth at each measurement time.

5. The apparatus of claim 1, wherein the act to generate the depth comprises applying an equal interval K-space transform and an inverse Fourier transform to the measurement data at each measurement time to produce the depth.

6. The apparatus of claim 1, wherein the act to generate the raw tomographic image comprises taking the raw tomographic image as a first depth matrix,
circularly shifting rows or columns of the first depth matrix per measurement time to generate a second depth matrix, and
generating the result tomographic image by subtraction of the first depth matrix and the second depth matrix.

7. The apparatus of claim 6,
wherein the act to generate the raw tomographic image shifts the rows or columns of the first depth matrix one by one to generate the second depth matrix.

8. The apparatus of claim 6,
wherein the act to generate the raw tomographic image shifts the rows or columns of the first depth matrix two by two to generate the second depth matrix.

9. In an information processing apparatus to generate a frequency domain optical coherence tomography image, which is connected with an optical coherence tomography device,
(a) controlling the optical coherence tomography device to shift a measurement point to a next adjacent measurement point at each measurement time and to acquire a measurement data at each measurement time by sending a control command to move a galvanometer of the optical coherence tomography device,
(b) receiving the measurement data from a spectrometer of the optical coherence tomography device,
(c) generating a depth based on the measurement data,
(d) generating, by the information processing apparatus, a raw tomographic image from the depth, and
(e) generating, by the information processing apparatus, a result tomographic image by reducing noise from the raw tomographic image,
wherein the step of generating the result tomographic image comprises subtracting the depth at each measurement time from the depth generated at another measurement time adjacent to said each measurement time, and
wherein the result tomographic image is an image in which the fixed pattern noise of the raw tomographic image is reduced.

10. The method of claim 9,
wherein the result tomographic image is an image in which fixed pattern noise of the raw tomographic image is reduced.

11. The method of claim 9,
wherein the step of generating the depth comprises applying an equal interval K-space transform and an inverse Fourier transform to the measurement data at each measurement time to produce the depth.

12. The method of claim 9,
wherein the step of generating the raw tomographic image comprises taking the raw tomographic image as a first depth matrix,
circularly shifting rows or columns of the first depth matrix per measurement time to generate a second depth matrix, and
generating the result tomographic image by subtraction of the first depth matrix and the second depth matrix.

* * * * *